United States Patent [19]
Pedersen

[11] 4,089,652
[45] May 16, 1978

[54] DETECTION OF WATER IN OIL

[76] Inventor: August Bartold Pedersen, Llanover Cottage, Ockham Road South, East Horsley, Surrey, England

[21] Appl. No.: 796,107

[22] Filed: May 12, 1977

[30] Foreign Application Priority Data

May 12, 1976 United Kingdom ............... 19538/76

[51] Int. Cl.$^2$ ..................... G01N 33/18; G01N 33/22
[52] U.S. Cl. ............................. 23/230 HC; 23/230 R; 23/253 R
[58] Field of Search ......... 23/230 HC, 230 M, 230 R, 23/253 R, 259, 254 R, 232 R

[56] References Cited

U.S. PATENT DOCUMENTS

| 3,019,342 | 1/1962 | Brooke | 23/230 HC |
| 3,528,775 | 9/1970 | O'Hara et al. | 23/230 HC |
| 3,833,340 | 9/1974 | Jones | 23/230 HC |
| 3,873,271 | 3/1975 | Young et al. | 23/230 HC |
| 3,976,572 | 8/1976 | Reick | 23/230 HC |

Primary Examiner—R.E. Serwin
Attorney, Agent, or Firm—Charles A. Huggett; Malcolm Keen

[57] ABSTRACT

A method of detecting water in an oil comprises bringing a sample of the oil into contact with a substance which is chemically inert to the oil but reactive with water to produce gas. The amount of gas produced is measured by the displacement of liquid from a closed vessel. Convenient forms of apparatus for carrying out the method are disclosed.

5 Claims, 3 Drawing Figures

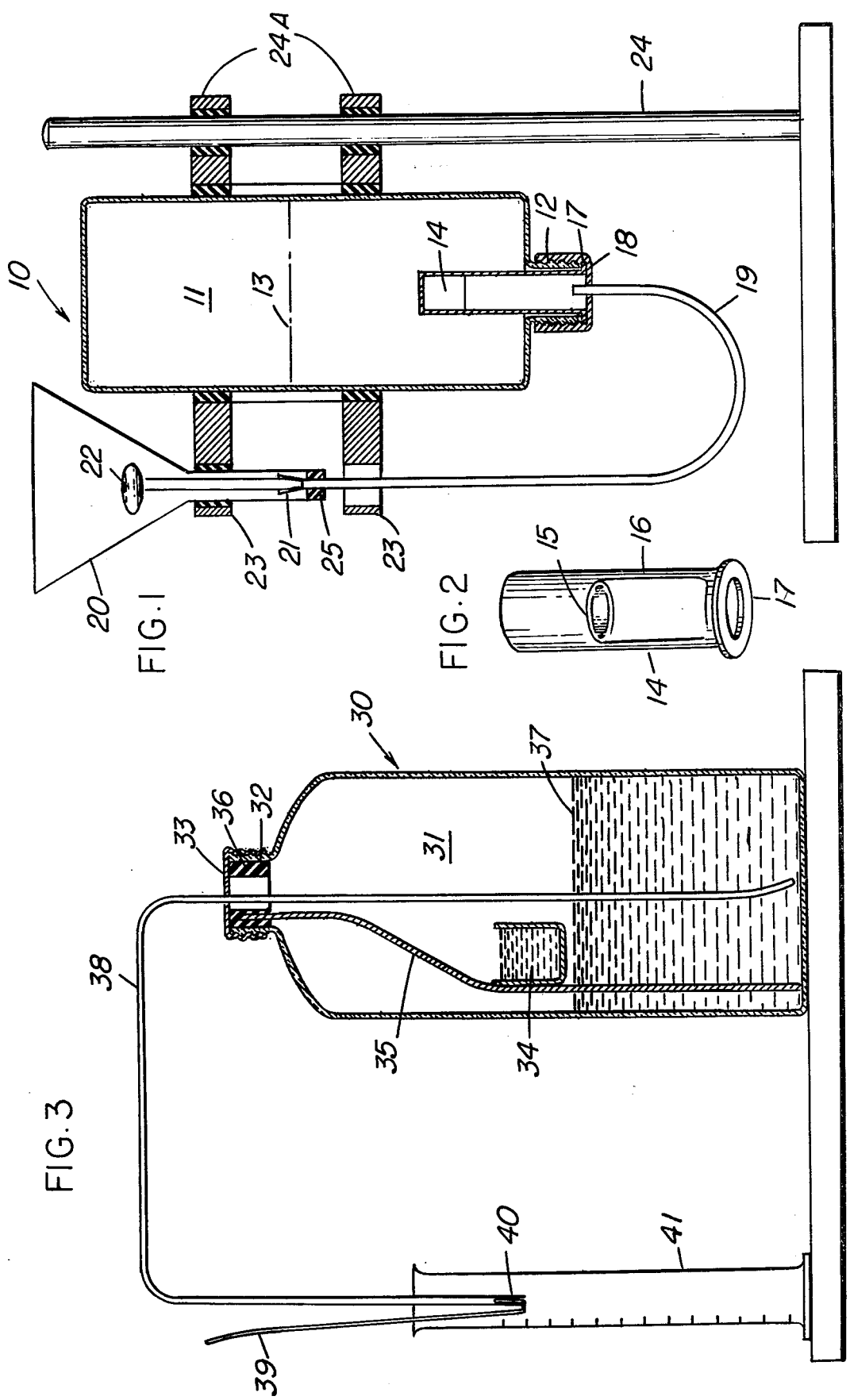

DETECTION OF WATER IN OIL

The present invention relates to the detection of water in oil and more particularly to the detection of minor proportions of water in petroleum oil products, for instance lubricating oil which has been used in a marine diesel engine.

BACKGROUND OF THE INVENTION

During the operation of a marine diesel engine, the circulating lubricant generally becomes contaminated with water. The effective working life of the lubricant is limited by the accumulation of water, which, apart from altering the lubricant properties of the oil, may have a deleterious effect on the metal to be lubricated. Similar considerations arise with other uses of oils.

In order to determine whether the oil is suitable for further use or for regeneration or rejection, it is frequently necessary to know whether water is present in the oil in excess of a predetermined tolerated proportion. Such a proportion might be in the region of a few percent, e.g. 1 to 5 percent by weight of wet lubricant, but substantially higher water contents can be encountered. On the other hand, it may be desired to apply a more stringent standard, of a fraction of one percent.

Devices are known by means of which the water content of an oil can be determined. For instance, a measured amount of oil may be confined in a closed vessel incorporating a pressure gauge together with a substance which reacts with water to produce gas. The amount of water present in the oil is then determined according to the pressure rise shown on the gauge. The oil may also be contacted in a vessel with a water-reactive substance and a carrier. The amount of produced gas is then measured by means of a separate manometer U-tube equipped with another manometric liquid and connected to the vessel, measuring the internal pressure developed.

SUMMARY OF THE INVENTION

I have now devised an improved method and apparatus for providing directly an indication of the water content of a sample oil in a manner capable of effective use by an unskilled operator. The indication may be in the form of a simple "go or no go" criterion or in the form of an explicit percentage reading. The results are in the typical case where the water is present in the oil in a highly emulsified state and are more reliable than those previously obtainable by other techniques.

The invention is based on the use of the same body of a liquid which is miscible with the oil, both as a medium for bringing the water and a reactive substance into intimate contact, and as the manometric or measuring liquid.

According to the present invention the method of detecting water in the oil comprises bringing a sample of the oil into contact with reagent means chemically inert to oil but reactive with water to produce gas, in a quantity of inert liquid which is miscible with the oil sample. The inert liquid is also used to represent the volume of gas produced if water is present in the sample.

The oil sample is preferably introduced or washed into the inert liquid by inverting a bottle containing the oil in an open-topped reservoir above a quantity of the inert liquid.

The apparatus for detecting water in the oil by this method comprises a bottle which can be inverted, means for releasing a predetermined sample of oil into the contents of the bottle as it is inverted, closure means for the bottle incorporating a narrow tube communicating therethrough at one end with the contents of the bottle, the other end of the tube being fitted with a removable plug and a calibrated vessel for receiving liquid transmitted through the tube.

Means may be provided for detachably locating a receiving vessel suitably in the form of a funnel in an upright position with the tube depending from it, alongside the inverted bottle on a stand. A reference mark on the tube, e.g. the junction between vessel and tube is brought opposite a marked level on the bottle so that the tube is suspended from vessel and bottle in the manner of a manometric U-tube. The volume of gas produced is then proportional to the rise of liquid in the tube.

Alternatively, both the bottle and the receiving vessel may be separately free-standing in their upright positions, e.g., on a table, with the tube coming from the top of the bottle. The tube enters and extends into the upper portion of a receiving vessel (e.g. a graduated cylinder), preferably to a level no further down than a marked reference level on the bottle. The apparatus has associated with it a supply of substance reactive with water, conveniently in capsule form, each capsule containing enough reagent to consume all the water that may be encountered. A supply of inert liquid is also provided, generally in an amount sufficient to half fill the bottle for each test.

BRIEF DESCRIPTION OF THE DRAWINGS

FIG. 1 is a sectional elevation of the detection apparatus while in use,

FIG. 2 is a view of a sample reservoir, and

FIG. 3 is a sectional elevation of another type of detection apparatus, while in use.

DESCRIPTION OF PREFERRED EMBODIMENTS

The invention finds particular application in the testing of marine diesel-engine oil, and the apparatus of the invention is valuable and convenient as an accessory on board ship for routine oil testing. The invention is also useful or checking the water contents of oil from pipeline test stations, including crudes and refined products e.g. fuels.

The sample of oil subjected to test need not be large, in spite of the small quantities of water likely to be encountered. Typically, a sample of 5 milliliters is acceptable.

The substance reactive with water to produce gas is preferably calcium hydride, although other substances may be used such as calcium carbide, sodium hydride and so forth. The substance must be chemically inert to the oil under test and also to the manometric or measuring liquid miscible with the oil.

The liquid miscible with the oil under test, especially when the latter is marine engine lubricant, is most conveniently a petroleum hydrocarbon liquid, for example, kerosine. Although other inert liquids miscible with the test oil may also be used, e.g. chlorinated hydrocarbons, oxygenated materials such as esters, ethers, polyolefins and so forth, the inert liquid should have a low vapor pressure, consistent with its use as a manometric liquid or measurer of gas volume. The quantity used is predetermined for the sake of reference level, but the amount is not otherwise critical.

The volume of the bottle should be sufficiently large in relation to that of the tube, so that the effect of the latter on the accuracy of the measurement can be neglected in comparison with the effect on the measurement of the volume of gas which may be produced. The effective volume of the tube may be decreased if necessary by the insertion therein of a core such as a wire.

The bottle may be any container with a closable upper opening and means such as transparent or translucent sides for observing the level of liquid in the bottle. The bottle may thus suitably be a conventional transparent plastics bottle with a screw-on cap. The opening receiving the screw-on cap may be plain or it may have a peripheral surface capable of receiving a flange on an oil sample reservoir holder whereby the reservoir may be clamped thereon by the cap. Alternatively, the opening may have an internal shoulder or other device to cooperate with the reservoir holder.

The means for releasing a predetermined sample of the oil under test into the bottle is preferably a reservoir adapted to hold a predetermined sample of oil, for instance in an open cup, suspended from the opening or otherwise supported within the bottle in its upright position, above the level of the miscible fluid such as kerosine. Inversion of the bottle will permit the miscible fluid to flush the oil sample out of the cup and mix thoroughly with it.

The closure means for the bottle, preferably the screw-on cap, above mentioned, incorporates a length of flexible tube passing through and sealed to the closure means so that when the cap is secured in place on the bottle, the internal bore of the tube, which is for instance of the order of ⅛-inch or less, communicates with the interior of the bottle. The length of the tube is not critical but it is preferably not substantially longer than is demanded for its manipulation. The tube is preferably made integral with the bottle cap. The movable plug is to be of dimensions suitable for manual insertion to block the end of the tube and may suitably be a rod or thick wire of appropriate diameter.

In the embodiment employing a funnel as receiving vessel a 60° conventional glass or plastics funnel of about 3-inches diameter with a stem of about 2-inches length is generally suitable. In the case of a graduated cylinder, a conventional one of 100 – 200 ml capacity is normally appropriate, depending upon the range of moisture content contemplated.

Referring to FIG. 1, the apparatus generally designated to comprise a bottle 11 of about 250 to 500 ml capacity initially in the upright position with its screw-top opening 12 uppermost, is filled in that position with kerosine up to mark 13. The bottle is preferably cylindrical to minimize distortion under pressure. A capsule of powdered calcium hydride or other water-reactive material is added to the kerosine and the bottle is left open for about 3 minutes, with occasional shaking. The kerosine is thereby dried.

The sample reservoir 14 will illustrate separately in FIG. 2 is shown inverted in FIG. 1 and consists of a cup 15 with means 16 for suspending it stiffly from the neck of the bottle. A flange 17 on the cupholder is adapted for confinement between the top edge of the bottle neck and the bottle cap 18 when the latter is screwed on, with suitable gaskets. A check is made to ensure that the gaskets and flanges are entirely clean.

The reservoir 14 is inserted and mounted in the upright bottle 11, and the reservoir cup 15 filled with a predetermined amount, such as 5 ml., of well shaken oil to be tested.

The cap 18 is then secured tightly on to the bottle. Cap 18 is joined to and penetrated by a narrow gauge flexible tube 19 which has a funnel 20 connected to its other end 21. A plug 22 is next inserted through the funnel to close the end 21.

The funnel is next placed in a retaining clip 23 which is attached to the bottle, and the bottle is inverted into the orientation depicted in FIG. 1 and shaken for about 2 minutes. The kerosine flushes the sample oil out of reservoir cup 15 and the calcium hydride dispersed in the kerosine intimately contacts any water present in the oil, which has dissolved in the kerosine. Reaction between the calcium hydride and water produces hydrogen which accumulates in the air above the kerosine.

The bottle is now placed on stand 24 with the aid of clips 24A with the cap lowermost and tube 19 forming a U-tube, as shown in FIG. 1, and allowed to stand for about 2 minutes. The junction 25 between the tube and the funnel stem should be adjusted in height to the level of the liquid in the bottle. It is convenient if mark 13 is half-way up the bottle, in which case this adjustment can be made earlier by lining up junction 25 with mark 13.

The plug 22 is then removed. If there was no water in the oil sample, the quantity of gas in the system will have remained unaltered. Since the amount of liquid in the bottle 1 remains substantially the same, the relative proportion entering the narrow tube being negligible, the volume of gas remains substantially the same. It was initially at atmospheric pressure and is thus again at atmospheric pressure when the level of the kerosine in the tube reaches and stays at the point 25 level with the kerosine in the bottle.

However, if there was water in the oil sample the calcium hydride dispersed in the kerosine will have reacted with it to produce gas, and consequently the kerosine level will rise into the funnel stem. In the event of an unexpectedly high rise in kerosine level the funnel can accommodate the excess in its divergent upper part. The stem of the funnel may be marked with a critical 'go no-go' limiting line, or it may be calibrated in percent water content gradations.

In FIG. 3 the apparatus 30 comprises a bottle 31 which may be similar to that of FIG. 1, likewise having a screw-top opening 32 and screw cap 33. The oil sample reservoir, however, takes the form of a cup 34 welded to a rod 35 which is fixed to a collar 36 removably located in the bottle neck. The reservoir stands on the bottom of the bottle with cup 34 above marked liquid level 37. The tube 38 which passes through cap 33 descends into the lower portion of the bottle.

This embodiment is used in a manner similar to that described for FIG. 1, except that the bottle is returned to its upright position after the oil sample has been properly mixed into the inert liquid (by inversion and shaking) and reacted and before the plug 39 is withdrawn from the end 40 of tube 38 remote from bottle 31. If water was present in the oil, the inert liquid will be driven from the bottle when plug 39 is withdrawn, through tube 38 into the graduated cylinder 41 where it can be measured as a direct indication of gas volume produced by the water. Tube 38 is sufficiently short and narrow so that the method gives satisfactorily accurate results. This embodiment has the advantage of extra simplicity over the embodiment first described; the bottle and cylinder being simply stood on a bench or table.

The whole apparatus or parts of it may be suitably fabricated in a translucent plastics material such as polyethylene.

I claim:

1. A method of detecting water in a sample of oil, which comprises:
   i. bringing the sample of oil into contact with reagent means chemically inert to the oil and reactive with water to produce gas, the reagent means being present in a quantity of an inert liquid miscible with the oil and contained in container fitted with a manometer tube communicating with the interior of the container,
   ii. determining the volume of the inert liquid driven out of the container by the gas generated by the reagent means.

2. A method according to claim 1 in which the reagent means comprises calcium hydride.

3. A method according to claim 1 in which the manometer tube extends into the upper portion of the container above the level of the inert liquid and in which the container is inverted to drive the inert liquid out of the container.

4. A method according to claim 1 in which the manometer tube extends into the lower portion of the container below the level of the inert liquid.

5. A method according to claim 1 in which the inert liquid comprises kerosine.

* * * * *